(12) United States Patent
Wachter et al.

(10) Patent No.: US 6,497,863 B1
(45) Date of Patent: Dec. 24, 2002

(54) DEODORIZING PREPARATIONS

(75) Inventors: Rolf Wachter, Dusseldorf (DE); Ute Griesbach, Dusseldorf (DE); Bernd Fabry, Korschenbroich (DE); Rolf E. Engstad, Tromso (NO)

(73) Assignee: Biotec Pharmacon ASA, Tromso (NO)

( * ) Notice: Subject to any disclaimer, the term of this patent is extended or adjusted under 35 U.S.C. 154(b) by 0 days.

(21) Appl. No.: 09/958,057

(22) PCT Filed: Apr. 11, 2000

(86) PCT No.: PCT/EP00/03192

§ 371 (c)(1),
(2), (4) Date: Feb. 8, 2002

(87) PCT Pub. No.: WO00/62752

PCT Pub. Date: Oct. 26, 2000

(30) Foreign Application Priority Data

Apr. 20, 1999 (DE) .................................... 199 17 743

(51) Int. Cl.[7] .......................... A61K 7/32; A61K 7/00; A61K 35/78; A61K 25/00; A61K 31/715; A01N 25/00

(52) U.S. Cl. ................. 424/65; 424/400; 424/401; 424/404; 424/405; 424/195.16; 514/54

(58) Field of Search .................... 424/65, 400, 401, 424/195.16, 404, 405; 514/54

(56) References Cited

U.S. PATENT DOCUMENTS

| | | |
|---|---|---|
| 3,659,025 A | 4/1972 | Halleck |
| 4,012,333 A | 3/1977 | Towle |
| 5,653,967 A | 8/1997 | Murphy |

FOREIGN PATENT DOCUMENTS

| | | |
|---|---|---|
| EP | WO9716164 | 5/1997 |

*Primary Examiner*—Shelley A. Dodson
(74) *Attorney, Agent, or Firm*—Ladas & Parry

(57) ABSTRACT

The invention relates to novel deodorizing preparations that have an effect that is enhanced by synergy and that contain (a) water-soluble β-(1,3)-glucans that are substantially free from β-(1,6) links, (b) aluminum chlorohydrate, (c) esterase inhibitors and/or (d) bactericidal or bacteriostatic active substances.

8 Claims, No Drawings

DEODORIZING PREPARATIONS

FIELD OF THE INVENTION

The invention belongs to the field of deodorising preparations which contain selected polysaccharides of the type β-(1,3) glucans; aluminium chlorohydrate, esterase inhibitors and/or bactericidal, respectively bacteriostatic, active agents, and the use of the particular glucans for the manufacture of deodorising praparations.

PRIOR ART

In the area of body, care deodorants are used for elimination of troublesome body odours. These odours are developing during the bacterial decomposition of sweat
which as such is odourless—especially in the humid and warm axillas or by similar conditions which offer the micro organisms good living conditions. Body odours can be masked by means of suitable odour substances. They can also be combated by use of preparations which inhibit the sweat secretion as such or which inhibit the decomposition of the sweat (so-called antihidrotica, antiperspirants or antitranspirants). Typical examples of such substances are aluminium compounds such as aluminium sulphate or aluminium chlorohydrate, zinc salts an citric acid compounds. A survey with regard to this can e.g. be found in Umbach (ed.) "*Kosmetik*", p. 141f, Thieme Verlag, Stuttgart/FRG, 1988.

From the experience of everyday life it is, however, evident that the problem of odour inhibition, especially by high temperatures or substantial activity, is not completely solved. The products on the market cannot permanently prevent the emission of sweat or the formation of odours. In fact the inhibition is limited in time and dependent on the amount of sweat which is discharged.

In this connection reference is made to the U.S. Pat. No. 5,223,491, which suggests to employ a carboxymethylated β-1,3 glucan, which has been extracted from the yeast fungus *Saccharomyces cerevisiae*, for topical application. The glucan is, however, insoluble in water and can accordingly only be formulated with great difficulties. From the teachings in the two papers DE-A1 3744345 (Lomapharm) and EP-B1 0175667 (Lam) are glucans well suited for stimulation of the activity of the macrophages. The pharmaceutical effect of different glucans is further known from the two European patent applications EP-A1 045338 (Debat) and EP-A1 0561408 (Kaken). Object of the European patent EP-B1 0500718 (Donzis) is the use of water insoluble β-(1,3) glucans, which are obtained from the cell walls of yeast, for revitalisation of the skin.

Therefore there is a continuous need for products which in regard to the minimisation of the secretion of sweat and attenuation of odour are enhanced and at the same time feature an increased skin cosmetic tolerance, i.e. a lowered potential of irritation in relation to especially sensible skin. The object of the invention was therefore to make such products available.

DESCRIPTION OF THE INVENTION

The object of the invention are deodorising preparations, containing
(a) water soluble β-(1,3) glucans, which are substantially free from β-(1,6) linkages,
(b) aluminium chlorohydrate,
(c) esterase inhibitors, and/or
(d) bactericidal, respectively bacteriostatic, agents.

A further object of the invention is the use of water soluble β-(1,3) glucans, which are substantially free from β-(1,6) linkages, for the manufacture of deodorising preparations.

The use of aluminium chlorohydrates, esterase inhibitors (e.g. triethyl citrate) and bactericidal active agents (e.g. chitosan) for preparation of deodorising and/or sweat inhibiting preparations is known from the state of the art. Surprisingly it was found that the particular glucans inhibit the activity of esterolytic enzymes already in the low ppm area, and that together with the above mentioned components a synergistic effect is achieved. The polysaccharides have a selective effect on serine esterases, respectively serine proteases, without disturbing the biological equilibrium of the skin flora. At the same time the use of glucans leads to a immunestimulation and an improvement of the skin cosmetic compatibility of the products, which means that they also can be used in cosmetic preparations.

Water Soluble β-(1,3) Glucans

The term glucans means homopolysaccharides based on glucose. Depending on sterical linking there is a difference between β-(1,3), β-(1,4) and β-(1,6) glucans. β-(1,3) Glucans normally show a helical structure, whereas glucans with a (1,4) linkage generally have a linear structure. The β-glucans of the invention have a (1,3) structure, i.e. they are substantillay free from undesired (1,6) linkages. Preferably such β-(1,3) glucans are used where the side chains exclusively show (1,3) linkages. Especially the agents contain glucans which are obtained on the basis of yeasts from the family Sacchaomyces, especially *Saccharomyces cerevisiae*. Glucans of this type are available in technical amounts according to known methods. The international patent application WO 95/30022 (Biotec-Mackzymal) describes a method for producing such substances, wherein glucans with β-(1,3) and β-(1,6) linkages are brought in contact with β-(1,6) glucanases in such a way, that practically all β-(1,6) linkages are loosened. Preferably used for the manufacture of these glucans are glucanases based on *Trichodermia harzianum*. As to the manufacture and availability of the glucans contained in these agents, reference is made to the above cited publication. The glucans can be contained in the preparations in amounts of 0.1 to 5, preferably 0.2 to 5, and especially 0.5 to 1% by weight, based on the agents.

Aluminium Chlorohydrate

The aluminium chlorohydrates of component (b) are colourless, hygroscopic crystals, which easily melt in air, and which are obtained through evaporation of solutions of aluminium chloride in water. Aluminium chlorohydrate is used for manufacturing of perspiration inhibiting and deodorising preparations and has probably its effect through the partial closure or stick together of the perspiratory glands by means of precipitation of proteins and/or removal of moisture [see *J.Soc. Cosm.Chem.* 24, 281 (1973)]. Under the trade name Locron® of Hoechst AG, Frankfurt/FRG, an aluminium chlorohydrate is for example on the market, which corresponds to the formula $[Al_2(OH)_5Cl].2.5\ H_2O$, and use of this is especially preferred (see *J.Pharm.Pharmacol.* 26, 531 (1975)].

Esterase Inhibitors

By the presence of sweat in the axillary area extracellular enzymes—esterases, preferentially proteases and/or lipases—are formed by means of bacteria, and they are decomposing the esters contained in the sweat and thereby odour substances are set free. Esterase inhibitors of component (c), preferably trialkyl—citrates such as trimethyl citrate, tripropyl citrate, tributyl citrate and especially triethyl citrate (Hydagen® CAT, Henkel KGaA, Düsseldorf/FRG) inhibit the enzyme activity and thereby reduce the formation of odours. Probably the free acid is thereby set free through the cleavage of the citric acid ester, and this acid lowers the pH value of the skin so much that the enzymes thereby are inactivated through acylation. Further substances which can be used as estersase inhibitors are dicarboxylic acids and their esters, such as for example glutaric acid, glutaric acid monoethyl ester, glutaric acid diethyl ester, adipic acid, adipic acid monoethyl ester, adipic acid diethyl ester, malonic acid and malonic acid diethyl ester, hydroxy carboxylic acids and their esters, such as for example citric acid, malic acid, tartaric acid or tartaric acid diethyl ester.

Bactericidal, Respectively Bacteriostatic Active Agents

Bactericidal, respectively bacteriostatic, active substances of component (d), which influence the germ flora and kill sweat destroying bacterias or inhibit their growth, can also be contained in the preparations. Typical examples are especially chitosan and phenoxyethanol. 5-Chloro-2-(2,4-dichlorophenoxy)phenol has shown to have an especially good effect, and this product is marketed under the trade name Irgasan® by Ciba-Geigy, Basel/CH.

Commercial Applicability

The special β-(1,3) glucans have for the described application area shown to be enzyme inhibiting. They can therefore especially be used for manufacturing of deodorising preparations, whereby they are used alone or together with other deo active agents such as aluminium chlorohydrates, further esterase inhibitors and/or bactericidal, respectively bacteriostatic, active substances. The compositions can in a preferred embodiment of the invention contain the components (a) to (d) preferably in the following amounts, based on the solids content:

(a) 0.01 to 50, preferable 0.1 to 10, % by weight of water soluble β-(1,3) glucans, which are substantially free from β-(1,6) linkages, (b) 1.0 to 50, preferably 10 to 40, % by weight of aluminium chlorohydrate, (c) 0.01 to 20, preferably 1.0 to 5.0, % by weight of esterase inhibitors, and/or (d) 0.01 to 5, preferably 0.1 to 1.0, % by weight of bactericidal, respectively bacteriostatic, agents.

It is required that the sum of the stated amounts is 100% by weight. The stated amounts are in each case understood to be the active content of the components.

To be able to apply the active substances on the skin in an economical dosage which can be applied in an easy and cosmetic appealing manner, they are usually incorporated into basis formulations. As the most important basis components are to mention: Alcoholic and water/alcohol solutions, emulsions, gels, oils, masses of wax/fat, pin preparations and powder. Thus the preparations according to the invention for example can contain up to 60% by weight of low aliphatic alcohols, preferably ethanol, as well as organic acids such as glycolic acid. Further substances which can be used are hyperfatting agents, emulsifiers, antioxidants, talcum, silicic acid (e.g. as support for the aluminium chlorohydrate), as well as perfume oils, etheral oils, colouring substances, and—for spray applications—propellants such as for example propane or butane. The agents are preferably marketed as rollers (roll-on-emulsions), sticks, deo sprays or pumping sprays.

The cosmetic preparations may further contain as additional auxiliary and additional agents mild surfactants, oil bodies, pearl lustre waxes, consistency substances, thickening agents, polymers, silicone compounds, fats, waxes, stabilizing agents, biogenic active substances, agents against dandruff, film forming agents, swelling agents, UV light protection factors, hydrotropes, preservatives, insect repellents, self tanning agents, solubilizing agents, germ inhibiting agents, and suchlike.

Further Auxiliary and Additional Substances

Typical examples of suitable mild, i.e. especially skin compatible surfactants, are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, ethercarboxylic acids, alkyl oligoglucosides, fatty acid glucamides, alkylamido betaines and/or protein fatty acid condensates, the last mentioned preferably based on wheat proteins.

As oil bodies use can be made of for example Guerbet alcohols based on fatty alcohols with 6 to 18, preferably 8 to 10 carbon atoms, esters of linear $C_6$–$C_{22}$ fatty acids with linear $C_6$–$C_{22}$ fatty alcohols, esters of branched $C_6$–$C_{13}$ carboxylic acids with linear $C_6$–$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isosteayl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In additon esters of linear $C_6$–$C_{22}$ fatty acids with branched alcohols, especially 2-ethylhexanol, esters of hydroxycarboxylic acids with linear or branched $C_6$–$C_{22}$ fatty alcohols, especially dioctyl malate, esters of linear and/or branched fatty acids with polyvalent alcohols (such as e.g. propylene glycol, dimeric diol or trimeric triol) and/or Guerbet alcohols, triglycerides based on $C_6$–$C_{10}$ fatty acids, liquid mixtures of mono-/di-/triglycerides based on $C_6$–$C_{18}$ fatty acids, esters of $C_6$–$C_{22}$ fatty alcohols and/or Guerbet alcohols with aromatic carboxylic acids, especially benzoic acid, esters of $C_2$–$C_{12}$ dicarboxylic acids with linear or branched alcohols with 1 to 22 carbon atoms or polyols with 2 to 10 carbon atoms and 2 to 6 hydroxyl groups, plant oils, branched primary alcohols, substituted cyclohexanes, linear and branched $C_6$–$C_{22}$ fatty alcohol carbonates, Guerbet carbonates, esters of benzoic acid with linear and/or branched $C_6$–$C_{22}$ alcohols (e.g. Finsolv® TN), linear or branched, symmetrical or unsymmetrical dialkyl ethers with 6 to 22 carbon atoms in each alkyl group, ring opening products of epoxydated fatty acid esters with polyols, silicone oils and/or aliphatic or naphthenic hydrocarbons, such as e.g. squalan, squalen or dialkyl cyclohexanes, can be used As emulsifiers for example nonionic surfactants from at least one of the following groups may be used:

(1) Addition products of 2 to 30 moles ethylene oxide and/or 0 to 5 moles propylene oxide on linear fatty alcohols with 8 to 22 C atoms, on fatty acids with 12 to 22 C atoms and on alkyl phenols with 8 to 15 C atoms in the alkyl group;

(2) $C_{12/18}$ fatty acid mono- and diesters of addition products of 1 to 30 moles ethylene oxide and glycerol;

(3) glycerol mono- and diesters and sorbitan mono- and diesters of saturated and unsaturated fatty acids with 6 to 22 carbon atoms and their ethylene oxide addition products;

(4) alkyl mono- and oligoglycosides with 8 to 22 carbon atoms in the alkyl group and their ethoxylated analogues;

(5) addition products of 15 to 60 moles ethylene oxide on ricinus oil and/or hardened ricinus oil;

(6) polyol and especially polyglycerol esters, such as e.g. polyglycerol polyricinoleate, polyglycerol poly-12-hydroxy stearate or polyglycerol dimerate isostearate, and also mixtures of compounds from more of these classes of substances;

(7) addition products of 2 to 15 moles ethylene oxide on ricinus oil and/or hardened ricinus oil;

(8) partial esters based on linear, branched, unsaturated or saturated $C_{6/22}$ fatty acids, ricinolic acid and 12-hydroxy stearic acid and glycerol, polyglycerol, pentaerythrite, dipentaerythrite, sugar alcohols (e.g. sorbitol), alkyl glucosides (e.g. methyl glucoside, butyl glucoside, lauryl glucoside) as well as polyglucosides (e.g. cellulose);

(9) mono-, di- and trialkylphosphates as well as mono-, di- and/or tri-PEG alkylphosphates and their salts;

(10) wool wax alcohols;

(11) polysiloxane/polyalkyl/polyether copolymers or corresponding derivatives;

(12) mixed esters of pentaerythrite, fatty acids, citric acid and fatty alcohol according to DE 1165574 PS and/or mixed esters of fatty acids with 6 to 22 carbon atoms, methyl glucose and polyols, preferably glycerol or polyglycerol,

(13) polyalkylene glycols, as well as

(14) glycerol carbonate.

The addition products of ethylene oxide and/or of propylene oxide on fatty alcohols, fatty acids, alkyl phenols, glycerol mono- and diesters as well as sorbitan mono- and -diesters of fatty acids or on ricinus oil are known products which are commercially available. They are mixtures of homologous substances, with average degree of alkoxylation corresponding to the ratio of the amounts of the substances ethylene oxide and/or propylen oxide and substrate, with which the addition reaction is carried out. $C_{12/18}$ fatty acid mono- and diesters of addition products of ethylene oxide on glycerol are known from DE 2024051 PS as revertive fatting agents for cosmetic preparations.

$C_{8/18}$ alkyl mono- and oligoglycosides, their manufacture and their use is known from prior art. Their preparation can especially be carried out by reaction of glucose or oligosaccharides with primary alcohols having 8 to 18 C atoms. With regard to the glycoside residue both monoglycosides, where a cyclic sugar group is glycosidic bond to the fatty alcohol, and oligomeric glycosides with a degree of oligomerisation until preferably about 8, are suitable. The degree of oligomerization is then a statistical mean value, based on a distribution of homologous which is usual for such products of technical quality.

Zwitterionic surfactants can also be used as emulsifiers. The term zwitterionic surfactants is intended to mean such surface active compounds which in their molecule have at least one quaternary ammonium group and at least one carboxylate and one sulphonate group. Especially suitable zwitterionic surfactants are the so-called betaines such as the N-alkyl-N,N-dimethyl ammonium glycinates, for example the coco alkyldimethyl ammonium glycinate, N-acylaminopropyl-N,N-dimethyl ammonium glycinate, for example the coco acylaminopropyl dimethyl ammonium glycinate, and 2-alkyl-3-carboxylmethyl hydroxyethyl imidazoline with in each case 8 to 18 C atoms in the alkyl or acyl-groups, as well as the coco acylaminoethyl hydroxyethyl carboxymethyl glycinate. Especially preferred is that under the CTFA term cocamidopropyl betaine known fatty acid amide derivative. Also suitable emulsifiers are ampholytic surfactants. Ampholytic surfactants are such surface active compounds which in addition to a $C_{8/18}$ alkyl or acyl group in the molecule at least contain a free amino group and at least one —COOH or —SO$_3$H group and which can form inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylamidopropyl glycines, N-alkyltaurines, N-alkylsarcosines, 2-alkylaminopropionic acids and alkylamino acetic acids with in each case about 8 to 18 C atoms in the alkyl group. Especially preferable ampholytic surfactants are the N-coco alkylamino propionate, the coco acylamino ethylamino propionate and the $C_{12/18}$ acylsarcosine. In addition to the ampholytic, also quaternary emulsifiers can be used, of which ester salts of the type of esterquats, preferably methylquaternised di-fatty acid triethanolamine ester salts, are especially preferable.

As hyperfatting agents substances such as for example lanolin and lecithin as well as polyethoxylated or acylated lanolin and lecithin derivatives, polyol fatty acid esters, monoglycerides and fatty acid alkanolamides can be used, whereby the last mentioned at the same time act as foam stabilisers.

As exemplary pearl gloss waxes the following should be mentioned: Alkylene glycol esters, especially ethyleneglycol distearate; fatty acid alkanolamides, especially coco fatty acid diethanolamide; partial glycerides, especially stearic acid monoglyceride; esters of polyvalent, possibly hydroxysubstituted carboxylic acids with fatty alcohols with 6 to 22 carbon atoms, especially long chain esters of tartaric acid; fat substances, such as for example fatty alcohols, fatty ketones, fatty aldehydes, fatty ethers and fatty carbonates, wherein the sum of carbon atoms is at least 24, especially lauron and distearyl ethers; fatty acids such as stearic acid, hydroxystearic acid or behenic acid, ring opening products of olefine epoxides with 12 to 22 carbon atoms with fatty alcohols with 12 to 22 carbon atoms and/or polyols with 2 to 15 carbon atoms and 2 to 10 hydroxyl groups, as well as their mixtures.

As consistency givers preferably use is made of fatty alcohols or hydroxy fatty alcohols with 12 to 22 and preferably 16 to 18 carbon atoms and additionally partial glycerides, fatty acids or hydroxy fatty acids. A combination of these substances with alkyl oligoglucosides and/or fatty acid-N-methyl glucamides with the same chain length and/or polyglycerol-poly-12-hydroxy stearates is preferred.

Suitable thickening agents are for example polysaccharides, especially xanthan gum, guar-guar, agar-agar, alginates and methyl celluloses, carboxymethyl celluloses and hydroxyethyl cellulose, as well as higher molecular polyethylene glycol mono- and diesters of fatty acids, polyacrylates, (e.g. Carbopols® from Goodrich or Synthalenes® from Sigma), polyacrylamides, polyvinyl alcohol and polyvinyl pyrrolidone, surfactants such as for example ethoxylated fatty acid glycerides, ester of fatty acids with polyols such as for example pentaerythrite or trimethylolpropane, fatty alcohol ethoxytates with narrow distribution of homologous or alkyl oligoglucosides as well as elektrolytes such as sodium chloride and ammonium chloride.

Suitable cationic polymers are for example cationic cellulose derivatives, such as e.g. a quaternized hydroxyethyl cellulose, which is available under the name of Polymer JR 400® from Amerchol, cationic starch, copolymers of diallyl ammonium salts and acrylamides, quaternized vinylpyrrolidone/vinylimidazol polymers, such as e.g. Luviquat® (BASF), condensation products of polyglycols and amines, quaternized collagen polypeptides, such as for example lauryl dimonium hydroxypropyl hydrolyzed collagen (Lamequat®L/Grünau), quaternized wheat polypeptides, polyethylene imine, cationic silicone polymers, such as e.g. amidomethicones, copolymers of adipic acid and dimethylamino hydroxypropyl diethylenetriamine (Cartaretine®/Sandoz), copolymers of acrylic acid with dimethyl diallylammonium chloride (Merquat® 550/Chemviron), polyamino polyamides, such as e.g. described in FR 2252840 A, as well as their cross-linked water soluble polymers, cationic chitin derivatives such as for example quaternized chitosan, possibly microcrystalline distributed, condensation products of dihalogen alkyls, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from Celanese, quaternised ammonium salt polymers, such as e.g. Mirapol® A-15, Mirapol® AD-1, Mirapol® AZ-1 from Miranol.

As exemplary anionic, zwitterionic, amphoteric and non-ionic polymers the following can be used: Vinyl acetate/crotonic acid copolymers, vinyl pyrrolidone/vinyl acrylate copolymers, vinyl acetate/butyl maleate/isobornyl acrylate copolymers, methyl vinylether/maleic acid anhydride copolymers and their esters, non-cross-linked and with polyols cross-linked polyacrylic acids, acrylamido propyltrimethyl ammonium chloride/acrylate copolymers, octylacrylamide/methyl methacrylate/tert.-butylaminoethyl methacrylate/2-hydroxypropyl methacrylate copolymers, polyvinylpyrrolidone, vinylpyrrolidone/vinylacetate copolymers, vinylpyrrolidon/dimethylamino ethylmethacrylate/vinyl caprolactam terpolymers as well as possibly derivatized cellulose ethers and silicones.

Suitable silicon compounds are for example dimethyl polysiloxane, methylphenyl polysiloxane, cyclic silicones as well as amino, fatty acid, alcohol, polyether, epoxy, fluorine, glykoside and/or alkyl modified silicone compounds, which at room temperature can be in the liquid as well as in the resin state. A detailed survey of suitable volatile silicones can also be found in Todd et al., Cosm. Toil. 91, 27 (1976).

Typical exemplary fats are glycerides, and as waxes natural waxes among others, can be used, such as e.g. candelilla wax, carnauba wax, Japan wax, espartogras wax, cork wax, guaruma wax, rice seed oil wax, sugar cane wax, ouricury wax, montan wax, beeswax, schellac wax, spermaceti, lanolin (wool wax), bürzel fat, ceresin, ozokerit (terrestrial wax), petrolatum, paraffin waxes, micro waxes; chemically modified waxes (hard waxes), such as e.g. montanester waxes, sasot waxes, hydrogenated yoyoba waxes as well as synthetic waxes, such as e.g. polyalkylene waxes and polyethylene glycol waxes.

As stabilizers metal salts of fatty acids, such as e.g. magnesium, aluminium and/or zinc stearate or ricinoleate can be used.

As biogenic active substances should be understood for example tocopherol, tocopherol acetate, tocopherol palmitate, ascorbic acid, desoxy ribonucleic acid, retinol, bisabolol, allantoin, phytantriol, panthenol, AHA acids, amino acids, ceramides, pseudoceramides, essential oils, extracts of plants and vitamin complexes.

As anti dandruff agents climbazol, octopirox and zinc pyrethion can be used. Useable film formation agents are for example chitosan, microcrystalline chitosan, quaternary chitosan, polyvinylpyrrolidone, vinylpyrrolidone/vinylacetate copolymers, polymers of the acrylic acids, quaternary derivatives of cellulose, collagen, hyaluronic acid or its salts and similar compounds.

As swelling agents for aqueous phases montmorillonite, clay mineral substances, pemulen, as well as alkylmodified Carbopol types (Goodrich) can be used. Further suitable polymers or swelling agents can be found in the survey of R.Lochhead in Cosm. Toil. 108, 95 (1993).

UV light protection factors are e.g organic substances (light protection filters) which at room temperature are in liquid or crystalline form, and which are capable of absorbing ultraviolet radiation and to set free the received energy in the form of radiation with long wavelength, e.g. in the form of heat. UVB filters can be soluble in oils or in water. As oil soluble substances the following are mentioned as examples:

3-Benzyliden camphor, respectively 3-benzylidene norcamphor and the derivatives thereof, e.g. 3-(4-methylbenzylidene)camphor as described in EP-B1 0693471;

4-aminobenzoic acid derivatives, preferably 4-(dimethylamino)benzoic acid 2-ethylhexyl ester, 4-(dimethylamino)benzoic acid 2-octyl ester and 4-(dimethylamino)benzoic acid amyl ester;

esters of cinnamonic acid, preferably 4-methoxy cinnamonic acid 2-ethylhexyl ester, 4-methoxy cinnamonic acid propyl ester, 4-methoxy cinnamonic acid isoamyl ester, 2-cyano-3,3-phenyl cinnamonic acid 2-ethythexylester (octocrylene);

esters of salicylic acid, preferably salicylic acid 2-ethylhexyl ester, salicylic acid 4-isopropyl benzyl ester, salicylic acid homomenthyl ester;

derivatives of benzophenone, preferably 2-hydroxy-4-methoxy benzophenone, 2-hydroxy-4-methoxy-4'-methyl benzophenone, 2,2'-dihydroxy-4-methoxy benzophenone;

esters of benzalmalonic acid, preferably 4-methoxy benzmalonic acid 2-ethylhexyl ester, triazine derivatives, such as e.g. 2,4,6-trianilino-(p-carbo-2'-ethyl-1'-hexyloxy)-1,3,5-triazine and octyltriazone, as described in EP A1 0818450;

propane-1,3-diones, such as e.g. 1-(4-tert.-butylphenyl)-3-(4'-methoxy-phenyl)-propane-1,3-dion;

ketotricyclo(5,2,1,0)-decane derivatives, as described in EP 0694521 B1.

As water soluble substances the following can be mentioned:

2-Phenylbenzimidazol-5-sulphonic acid and the alkali, alkaline earth, ammonium, alkylammonium, alkanolammonium and glucammonium salts;

sulphonic acid derivatives of benzophenones, preferably 2-hydroxy-4-methoxybenzophenon-5-sulphonic acid and their salts;

sulphonic acid derivatives of 3-benzylidene camphor, such as e.g. 4-(2-oxo-3-bornylidenmethyl)-benzene sulphonic acid and 2-methyl-5-(2-oxo-bornylidene)sulphonic acid and their salts.

As typical UV-A filters especially derivatives of benzoyl methane come in question, such as e.g. 1-(4'-tert.-butylphenyl)-3-(4'-methoxyphenyl)propane-1,3-dion, 4-tert.butyl-4'-methoxydibenzoyl-methane (Parsol 1789), or 1-phenyl-3-(4'-isopropylphenyl-propane-1,3-dion. The UV-A and UV-B filters can of course also be used in mixtures. In addition to the mentioned soluble substances also insoluble light protection pigments can be used for this purpose, i.e. fine disperse metal oxides or salts. Examples of suitable metal oxides are especially zinc oxide and titanium dioxide and in addition other oxides of iron, zirconium, silicon, manganese, aluminium and cerium, as well as their mixtures. As salts silicates (talk), barium sulphate or zinc stearate can be used. The oxides and salts are used in the form of the pigments for skin caring and skin protecting emulsions and decorative cosmetics. The particles should have an average diameter of less than 100 nm, preferably between 5 and 50 nm and especially between 15 and 30 nm. They can have a spherical shape, but particles can also be used which have an ellipsoidal form or else have a shape which differs from the spherical shape. In sun protecting agents preferably so-called micro or nano pigments are used. Preferably micronized zinc oxide is used.

Further suitable UV light protection factors can be found in the survey by P.Finkel in SÖFW-Journal 122, 543 (1996).

In addition to the primary light protection substances mentioned above, also secondary light protection substances of the antioxidant type find use, which interrupt the photochemichal reaction chain, which is initiated when UV radiation penetrates the skin. Typical examples of such are amino acids (e.g. glycine, histidine, tyrosine, tryptophane) and their derivatives, imidazoles (e.g. urocaninic acid) and their derivatives, peptides such as D,L-camosine, D-camosine, L-camosine and their derivatives (e.g. anserine), carotinoides, carotine (e.g. α-carotin, β-carotin, lycopin) and their derivatives, chlorogenic acid and its derivatives, liponic acid and its derivatives (e.g. dihydroliponic acid), aurothioglucose, propylthiouracil and other thiols (e.g. thioredoxin, glutathion, cystein, cystin, cystamine and their glycosyl, n-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and their derivatives (esters, ethers, peptides, lipides, nucleotides, nucleosides and salts) as well as sulfoximine compounds (e.g. buthionin sulfoximines, homocystein sulfoximines, butionin sulfones, penta-, hexa-, hepta-thionin sufoximine) in very small compatible doses (e.g. pmol to µmol/kg), further (metal) chelating agents (e.g. α-hydroxy fatty acids, palmitic acid, phytinic acid, lactoferrine), α-hydroxy acids (e.g. citric acid, lactic acid, malic acid), humin acid, bile acid, bile extracts, bilirubin, bifiverdin, EDTA, EGTA and their derivatives, unsaturated fatty acids and their derivatives (e.g. γ-linolenic acid, linolic acid, oleic acid), folic acid and their derivatives, ubichinon and ubichinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A patmitate) as well as koniferyl benzoate of benzoe resin, rutinic acid and their derivatives, α-glycosylrutin, ferula acid, furfuryliden glucitol, carnosine, butylhydroxy toluene, butylhydroxy anisol, nordihydro guajak resin acid, nordihydro guajaret acid, trihydroxy butyrophenon, uric acid and their derivatives, mannose and its derivatives, super oxide dismutase, zinc and its derivatives (e.g. ZnO, $ZnSO_4$), selen and its derivatives (e.g. selen-methionin), stilbenes and their derivatives (e.g. stilbene oxide, trans-stilbene oxide), and the derivatives suitable according to the invention (salts, esters, ethers, sugars, nucleotides, nucleosides, peptides and lipids) of these mentioned active substances.

For improvement of the flow properties further hydrotropes, such as for example ethanol, isopropyl alcohol, or polyols can be used. Polyols which in this case can be used preferably have 2 to 15 carbon atoms and at least two hydroxyl groups. Typical examples are:

Glycerol;

alkylene glycols, such as for example ethylene glycol, diethylene glycol, propylene glycol, butylene glycol, hexylene glycol as well as polyethylene glycols with an average molecular weight from 100 to 1000 Daltons;

oligoglycerol mixtures of technical quality with a self-condensation degree of 1.5 to 10, such as e.g. technical quality diglycerol mixtures with a diglycerol content of 40 to 50% by weight;

methyol compounds, such as especially trimethylol ethane, trimethylol propane, trimethylol butane, pentaerythrite and dipentaerythrite;

low alkyl glucosides, especially such with 1 to 8 carbons in the alkyl residue, such as for example methyl and butyl glucoside;

sugar alcohols with 5 to 12 carbon atoms, such as for example sorbitol or mannit;

sugars with 5 to 12 carbon atoms, such as for example glucose or saccharose;

aminosugars, such as for example glucamine;

As preservatives for example phenoxyethanol, formaldehyde solution, parabene, pentanediol or sorbic acid as well as those mentioned in enclosure 6, parts A and B of the cosmetic regulation, are further classes of substances.

Typical examples of germ inhibiting substances are preservatives with specific effects against gram-positive bacteria, such as 2,4,4'-trichloro-2'-hydroxy diphenylether, chlorohexidin(1,6-di-(4-chlorophenyl-biguanido-hexan) or TCC (3,4,4'-trichlorocarbanilide). Many scent substances and etheral oils also have antimicrobial properties. Typical examples are the active agents eugenol, menthol and thymol in carnation, mint and thyme oil. An interesting natural deo substance is the terpene alcohol famesol (3,7,11-trimethyl-2,6,10-dodecatrien-1-ol), which is present in lime flower oil and has a smell of lilies of the valley. Also glycerol monolaurate have been used as bacteriostaticum. Normally the content of the further germ inhibiting agents is about 0.1 to 2% by weight, based on the solids content of the preparations.

As insect repellents N,N-diethyl-m-toluamide, 1,2-pentanediol or insect repellent 3535 come into question, as self tanning agent dihydroxy acetone is suited.

As perfume oils mixtures of natural and synthetic scent substances should be mentioned. Natural odour substances are extracts-of flowers (lilies, lavendel, roses, jasmin, neroli, ylang-ylang), stems and blades (geranium, patchouli, petitgrain), fruits (anis, coriander, caraway, juniper), fruit shells (bergamot, lemon, orange), roots (macis, angelica, celery, kardamon, costus, iris, calmus), wood (stone pine, sandel, guajac, cedar, rosewood), herbs and grass (tarragon, lemongrass, sage, thyme), needles and twigs (spruce, fir, pine, traipsed), resins and balsams (galbanum, elemi, benzoe, myrrh, olibanum, opoponax). Raw materials from animals are also possible, such as for example zibet and castoreum. Typical synthetic odour compounds are products from types of esters, ethers, aldehydes, ketones, alcohols and hydrocarbons. Odour compounds from types of esters are e.g. benzyl acetate, phenoxyethyl isobutyrate, p-tert.-butylcyclohexyl acetate, linalyl acetate, dimethylbenzyl carbinyl acetate, phenylethyl acetate, linalyl benzoate, benzyl formate, ethylmethylphenyl glycinate, allylcyclohexyl propionate, styrallyl propionate and benzyl salicylate. Benzylethyl ether belongs for example to the ethers, to the aldehydes e.g. the linear alkanales with 8 to 18 carbon atoms, citral, citronellal, citronellyl oxyacetaldehyde, cyclamen aldehyde, hydroxy citronellal, lilial and bourgeonal, to the ketones e.g. the ionones, α-isomethyl ionon and methylcedryl ketone, to the alcohols anethol, citronellol, eugenol, isoeugenol, geraniol, linalool, phenylethyl alcohol and terpineol; to the hydrocarbons mainly the terpenes and balsams belong. However, mixtures of different odour substances are preferred, which together give a pleasant smell. Also etheral oils with low volatility, which often are used as aroma components, are suited as perfume oils, e.g. sage oil, chamomile oil, carnation oil, melissa oil, mint oil, cinnamon leaf oil, limeflower oil, juniper berry oil, vetiver oil, oliban oil, galbanum oil, labolanum oil and lavandin oil. Preferably used are bergamot oil, dihydromyrcenol, lilial, lyral, citronellol, phenylethyl alcohol, α-hexylcinnamon aldehyde, geraniol, benzyl acetone, cyclamen aldehyde, linalool, boisambrene forte, ambroxane, indol, hedione, sandelice, lemon oil, mandarin oil, orange oil, allylamyl glycolate, cyclovertal, lavandine oil, muskateller sage oil, β-damascone, geranium oil bourbon, cyclohexyl salicylate, Vertofix coeur, iso-E-super, Fixolide NP, Evernyl, iraidein gamma, phenylacetic acid, geranyl acetate, benzyl acetate, rose oxide, romillate, irotyl and floramate, alone or in mixtures.

As colouring agents such substances which are suited and approved for cosmetic purposes can be used, such as for example those mentioned in the publication "Kosmetische Färbemittel" (cosmetic dyes) of the "*Farbstoffkommission der Deutschen Forschungsgemeinschaft*", published by Verlag Chemie, Weinheim, 1984, p. 81–106. These dyes are generally used in concentrations from 0.001 to 0.1% by weight, based on the whole mixture.

EXAMPLES

The effect of the agents according to the invention was determined by means of the esterase inhibition. For this purpose the rest activity after 15 minutes influence time of 0.1 to 5000 ppm of the test mixtures on the esterase was determined at pH=6 (adjustment with NaOH) parallel to a not inhibited control (standard=100%). The compositions 1 to 3 are according to the invention, the preparations V1 to V4 are comparison. Table 1 shows a summary of the examples performed (stated amounts in % by weight).

TABLE 1

Formulations and Esterase Inhibition

| Composition / performance | 1 | 2 | 3 | V1 | V2 | V3 | V4 |
|---|---|---|---|---|---|---|---|
| Betaglucan * | 0.5 | 0.5 | 0.5 | — | — | — | — |
| Aluminium chlorohtdrate | — | 50.0 | 50.0 | 50.0 | — | 50.0 | 50.0 |
| Triethyl citrate | — | 5.0 | 5.0 | — | 5.0 | 5.0 | — |
| Chitosan | — | — | 1.0 | — | — | — | 5.0 |
| Ethanol | 20.0 | 20.0 | 20.0 | 20.0 | 20.0 | 20.0 | 20.0 |
| Water | | | | ad 100 | | | |
| Esterase acivity [%] | | | | | | | |
| at 2000 ppm | — | — | — | 100 | 77 | 75 | 70 |

TABLE 1-continued

Formulations and Esterase Inhibition

| Composition / performance | 1 | 2 | 3 | V1 | V2 | V3 | V4 |
|---|---|---|---|---|---|---|---|
| at 500 ppm | — | — | — | — | 100 | 100 | 100 |
| at 100 ppm | 0 | 0 | 0 | — | — | — | — |
| at 10 ppm | 5 | 0 | 0 | — | — | — | — |
| at 1 ppm | 28 | 15 | 12 | — | — | — | — |
| at 0.1 ppm | 72 | 66 | 55 | — | — | — | — |

* Highcareen ® GS, Henkel KGaA, Düsseldorf / FRG

What is claimed is:

1. A deodorising preparation, comprising
   a. water soluble β-(1,3) glucans, which are substantially free from β-(1,6) linkages,
   b. aluminum chlorohydrate,
   c. esterase inhibitors, and/or
   d. bactericidal, respectively bacteriostatic, agents.

2. The preparation according to claim 1, wherein the preparation contains glucans which are obtained based on yeasts from the family Saccharomyces.

3. The preparation according to claim 1, wherein the preparation contains glucans which are obtained by contacting glucans having β-(1,3) and β-(1,6) linkages with β-(1,6) glucanases, in such a way that practically all β-(1,6) linkages are loosened.

4. The preparation according to claim 3, wherein the glucans previously have been treated with glucanases based on *Trichodermia harzianum*.

5. The preparation according to claim 1, wherein the preparation contains trialkyl citrates as esterase inhibitors.

6. The preparation according to claim 1, wherein the preparation contains chitosans as bactericidal, respectively bacteriostatic, active agents.

7. The preparation according to claim 1, wherein the preparation contains, based on the solids content,
   a. 0.01 to 50% by weight of water soluble β-(1,3) glucans, which are substantially free from β-(1,6) linkages,
   b. 1.0 to 50% by weight of aluminum chlorohydrate,
   c. 0.01 to 20% by weight of esterase inhibitors, and/or
   d. 0.01 to 5.0% by weight of bactericidal, respectively bacteriostatic, agents provided that the stated amounts are completed to 100% by weight.

8. Method for preparing deodorizing preparation comprising including water-soluble β-(1,3) glucans which are substantially free from β-(1,6) linkages in the preparation.

* * * * *